(12) United States Patent
Linz et al.

(10) Patent No.: US 8,372,974 B2
(45) Date of Patent: Feb. 12, 2013

(54) REGIOSELECTIVE PREPARATION OF SUBSTITUTED PYRIMIDINES

(75) Inventors: Guenter Linz, Mittelbiberach (DE); Adil Duran, Biberach (DE); Gerd Kraemer, Eberhardzell (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 12/933,125

(22) PCT Filed: Mar. 19, 2009

(86) PCT No.: PCT/EP2009/053266
§ 371 (c)(1),
(2), (4) Date: Oct. 25, 2010

(87) PCT Pub. No.: WO2009/115583
PCT Pub. Date: Sep. 24, 2009

(65) Prior Publication Data
US 2011/0060141 A1 Mar. 10, 2011

(30) Foreign Application Priority Data
Mar. 20, 2008 (EP) .................................... 08153119

(51) Int. Cl.
*C07D 239/02* (2006.01)
(52) U.S. Cl. ....................................... 544/330; 544/334
(58) Field of Classification Search .................. 544/332, 544/330, 310, 320, 321, 311
See application file for complete search history.

(56) References Cited

U.S. PATENT DOCUMENTS 7,122,670 B2 * 10/2006 Kath et al. ................... 544/330
7,928,109 B2    4/2011  Luzzio et al.
2011/0077403 A1 * 3/2011 Duran et al. ................. 544/332
2011/0190499 A1 * 8/2011 Linz et al. .................... 544/332
2012/0172596 A1   7/2012 Linz et al.

FOREIGN PATENT DOCUMENTS

| JP | 62000062 A * | 1/1987 |
| WO | 2005023780 A1 | 3/2005 |
| WO | WO 2006117560 A1 * | 11/2006 |
| WO | 2008071587 A2 | 6/2008 |
| WO | 2009115587 A1 | 9/2009 |
| WO | 2011018518 A1 | 2/2011 |

OTHER PUBLICATIONS

J. March, Advanced Organic Chemistry Reactions, Mechanisms and Structure 248-272 (4th ed., 1992).*
J. March, Advanced Organic Chemistry Reactions, Mechanisms and Structure 205, 352-357, 652-653 (4th ed., 1992).*
The Condensed Chemical Dictionary 822 (Gessner G. Hawley ed., 9th ed., 1977); Concise Chemical and Technical Dictionary 1081 (H. Bennett ed., 4th ed., 1986); Hawley's Condensed Chemical Dictionary 1186 (Richard J. Lewis, Sr. ed., 15th ed., 2007).*
Hawley's Condensed Chemical Dictionary 753 (R.J. Lewis, Sr. ed., 15th ed., 2007).*
R.G. Pearson, Journal of the American Chemical Society, 85, 3533-3539 (1963).*
H. Diringer et al., Journal of Medicinal Chemistry, 13, 151-152 (1970).*
International Search Report, Form PCT/ISA/210, for corresponding PCT/EP2009/053266; date of mailing: Aug. 19, 2009.
J. Leonard et al.; Advanced Practical Organic Chemistry; Second Edition; 1985; pp. 129-226.

* cited by examiner

*Primary Examiner* — James O Wilson
*Assistant Examiner* — Alexander R Pagano
(74) *Attorney, Agent, or Firm* — Michael P. Morris; Mary-Ellen M. Devlin

(57) ABSTRACT

The present invention relates to a method of making pyrimidines of formula (III), wherein X1, X2, R1 and R2 have the meanings as defined herein.

13 Claims, No Drawings

REGIOSELECTIVE PREPARATION OF SUBSTITUTED PYRIMIDINES

FIELD OF APPLICATION OF THE INVENTION

The present invention provides a new method for preparing selectively 2-amino-5-trifluoromethylpyrimidine derivatives which can be used as intermediates for the preparation of pharmacologically active compounds.

KNOWN TECHNICAL BACKGROUND/AIM OF THE INVENTION

In pyrimidine chemistry, for the majority of nucleophilic substitution reactions involving 2,4-functionalized pyrimidines and amines it is known that the first amine addition occurs preferentially (or exclusively) at the more reactive pyrimidine 4-position.

The reaction of pyrimidines of formula I' (where X is a leaving group; most commonly a halogen, particularly chlorine) and amines of formula II usually provides mixtures of regioisomers of formulae III' (2-amino pyrimidine derivatives) and IV' (4-amino pyrimidine derivatives) (see Scheme 1 below). Examples for such unselective reactions can be found in the art, inter alia, for the electron deficient 2,4-dichloro-5-trifluoromethylpyrimidine.

Scheme 1:

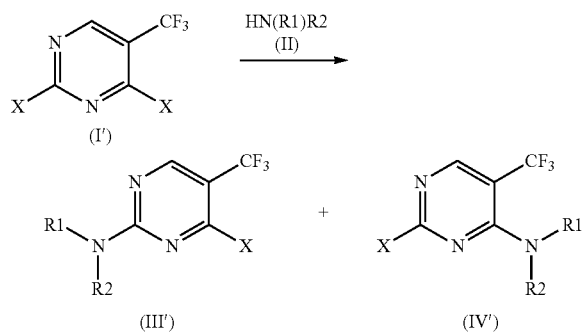

Thus, usually, the reactions of 2,4-dichloropyrimidine derivatives with amines provide non-selective mixtures of 2-chloro-4-amino-pyrimidines and isomeric 2-amino-4-chloropyrimidines in such that these reactions are of limited utility not only due to their lack of selectivity (and its impact on overall yield) but also because separation of the resulting isomers is generally extremely difficult and may require preparative HPLC, which is often not desired in a process sequence.

In contrast, there are only few examples where an amine is added to a 2,4-dichloropyrimidine in a selective manner to provide preferentially the 2-amino-4-chloropyrimidine. The most notable example of this type of reaction can be found in the international application WO 2005/023780 which describes a method for selective addition of an amine functionality to the C-2 position of a $CF_3$-substituted pyrimidine ring in the presence of a Lewis Acid (namely a salt of a metal ion) and a non-nucleophilic base.

However, there remains a need in the art for providing methods for obtaining efficiently compounds of formula III'. Further, there remains a need in the art for selective addition of amines to the usually less reactive C-2 position of pyrimidines which are substituted at C-5 position by $CF_3$. Further on, there remains a need in the art for efficient providing compounds of formula III' vis-à-vis unselective regioisomeric mixtures.

Other aims of the present invention will become apparent to the skilled man from the foregoing and following remarks.

DESCRIPTION OF THE INVENTION

It has now surprisingly been found, that by using a phenolate leaving group (advantageously said phenolate is electron deficient, e.g. by substitution with one or more electron-withdrawing functional groups on the phenyl ring), such as particularly the 4-nitrophenyloxy leaving group, or a N-oxide leaving group (preferably a heterocyclyl N-oxide or heteroaryl N-oxide leaving group, advantageously said heterocyclyl N-oxide or heteroaryl N-oxide leaving group is electron deficient, e.g. by substitution with one or more electron-withdrawing functional groups on the heterocyclyl or heteroaryl ring and/or by containing 1, 2, 3, 4 or more ring nitrogen atoms), such as particularly the benzotriazol-1-oxy leaving group, as X on the pyrimidine of formula I', one can selectively add an amine functionality to the C-2 position of the pyrimidine ring via nucleophilic aromatic substitution reaction without needing the presence of any Lewis acidic metal ion.

Further on, by reacting pyrimidine compounds of formula I', in which X is a leaving group selected from the group consisting of phenyloxy optionally substituted by 1-5 suitable substituents (particularly 4-nitrophenyloxy), heterocyclyl N-oxy optionally substituted by 1-5 suitable substituents, and heteroaryl N-oxy optionally substituted by 1-5 suitable substituents (particularly benzotriazol-1-oxy), with amines of formula II one can obtain selectively compounds of formula III'.

The invention thus relates to a process comprising a method of making a compound of formula III

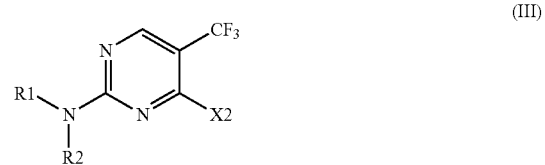

in which

X2 is a leaving group, such as phenyloxy optionally substituted by 1-5 suitable substituents, heterocyclyl N-oxy optionally substituted by 1-5 suitable substituents, or heteroaryl N-oxy optionally substituted by 1-5 suitable substituents; and R1 and R2 are substituents independently selected from the group consisting of hydrogen, an aromatic group and an aliphatic group; or taken together and with inclusion of the nitrogen atom, to which they are attached, form a 4-11 membered aromatic or aliphatic ring;

said method comprising reacting a compound of formula I

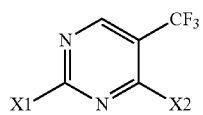

(I)

with an amine of formula II [HN(R1)R2] to form a compound of formula III, in which
X1 is a leaving group selected from the group consisting of:
phenyloxy optionally substituted by 1-5 suitable substituents,
heterocyclyl N-oxy optionally substituted by 1-5 suitable substituents, and
heteroaryl N-oxy optionally substituted by 1-5 suitable substituents.

In a more detailed embodiment of this method according the present invention, phenyloxy optionally substituted by 1-5 suitable substituents for use as leaving group in the meaning of the present invention may refer to phenyloxy independently substituted with 1-5 electron-withdrawing substituents on the phenyl ring, such as e.g. halo (particularly fluoro or chloro), nitro or the like.

In the context of this embodiment, illustrative examples of phenyloxy optionally substituted by 1-5 suitable substituents which may be used as leaving group in the meaning of the present invention include, without being restricted to, nitrophenyloxy like 2- or 4-nitrophenyloxy, and pentafluorophenyloxy, whereby 4-nitrophenyloxy is to be emphasized.

In another more detailed embodiment of this method according to the present invention, heterocyclyl N-oxy optionally substituted by 1-5 suitable substituents for use as leaving group in the meaning of the present invention may refer to mono- or fused bicyclic N-oxy imide derivatives.

In the context of this embodiment, illustrative examples of heterocyclyl N-oxy optionally substituted by 1-5 suitable substituents which may be used as leaving group in the meaning of the present invention include, without being restricted to, N-succinimidoxy and N-phthalimidoxy.

In another more detailed embodiment of this method according to the present invention, heteroaryl N-oxy optionally substituted by 1-5 suitable substituents for use as leaving group in the meaning of the present invention may refer to mono- or fused bicyclic N-oxy-azole derivatives or to mono- or fused bicyclic N-oxy-azinone derivatives.

In the context of this embodiment, illustrative heteroaryl N-oxy optionally substituted by 1-5 suitable substituents which may be used as leaving group in the meaning of the present invention include, without being restricted to, benzotriazol-1-oxy, 7-aza-benzotriazol-1-oxy and 1,2,3-benzotriazin-4(3H)-one-3-oxy, whereby benzotriazol-1-oxy is to be emphasized.

In a preferred embodiment of this invention, X1 and X2 are the same.

For example, X1 and X2 are the same and are each a leaving group selected from the group consisting of:
phenyloxy optionally substituted by 1-5 suitable substituents on the phenyl ring (such as e.g. nitrophenyloxy like 2- or 4-nitrophenyloxy, or pentafluorophenyloxy),
heterocyclyl N-oxy optionally substituted by 1-5 suitable substituents on the heterocyclyl ring (such as e.g. N-succinimidoxy or N-phthalimidoxy), and
heteroaryl N-oxy optionally substituted by 1-5 suitable substituents on the heteroaryl ring (such as e.g. benzotriazol-1-oxy, 7-aza-benzotriazol-1-oxy or 1,2,3-benzotriazin-4(3)-one-3-oxy).

In a more preferred embodiment of this invention, X1 and X2 are the same and are each 4-nitrophenyloxy.

It is to be understood that the 4-nitrophenyloxy radical within the meaning of this invention is of the following formula:

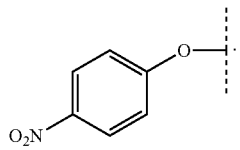

In another more preferred embodiment of this invention, X1 and X2 are the same and are each benzotriazol-1-oxy.

It is to be understood that the benzotriazol-1-oxy radical within the meaning of this invention is of the following formula:

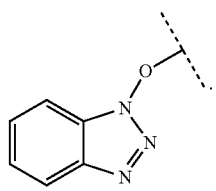

A particular aspect of the present invention is the abovementioned method characterized in that said reaction is performed as nucleophilic aromatic substitution reaction.

Another particular aspect of the present invention is the abovementioned method characterized in that said reaction is performed without the presence of a Lewis acidic metal ion.

Unless otherwise indicated, some terms used above and below to describe the compounds mentioned herein may be defined more closely as follows:

As used herein the term "aromatic", and specifically, an "aromatic group" refers to an aryl or heteroaryl radical as defined herein.

Further, an "aromatic amine" or "aromatic amine radical" refers to any amine or amine radical bound to at least one $sp^2$ carbon atom that is part of an aryl or heteroaryl group. An amine or amine radical will be referred to as an aromatic amine or radical even if the amine nitrogen is bound to a hydrogen or an $sp^3$ carbon atom, in addition to the one $sp^2$ carbon atom. Thus, for example, —HN($C_6$-$C_{10}$)aryl and —N(($C_1$-$C_6$)alkyl)(($C_6$-$C_{10}$)aryl) each refer to aromatic amine radicals as defined herein, despite the fact that each amine nitrogen is attached to non-aromatic substituents.

The term "aryl" refers to aromatic radicals such as phenyl, naphthyl, tetrahydronaphthyl, indanyl and the like. Unless otherwise mentioned, an "aryl" group may be optionally substituted with 1-3 suitable substituents, as defined herein. "Aryl" also refers to a phenyl radical fused to a non-aromatic heterocycle. Examples of such groups include but are not limited to 2-oxo-indolinyl, chromanyl, indolinyl and 2-oxo-3,4-dihydroquinolinyl optionally substituted by 1 to 3 suitable substituents.

As used herein, the term "heteroaryl" refers to an aromatic heterocyclic group usually with one heteroatom selected from O, S and N in the ring, wherein—unless otherwise mentioned—the aromatic heterocyclic group may be substituted by up to three suitable substituents as defined herein. In addition to said one heteroatom, the aromatic heterocyclic group may optionally have up to four N atoms in the ring. Examples of heteroaryl groups include but are not limited to pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, indolyl, and the like; optionally substituted by 1 to 3 suitable substituents. Alternatively, any ring carbon, —CH—, of the aforementioned heteroaryl group, may be replaced by a group selected from —C=O or —SO$_2$.

"Heteroaryl" also refers to one of the aforementioned heteroaryl groups fused to a non-aromatic heterocycle. Examples of such groups include but are not limited to 1,3-dihydro-pyrrolo[2,3-b]pyridin-2-one, 3,4-dihydro-1H-[1,8] naphthyridin-2-one, 1,3-dihydro-pyrrolo[2,3-b]pyridine and 3,4-dihydro-2H-pyrano[2,3-b]pyridine.

"Aliphatic", and specifically, an "aliphatic group" refers to an alkyl, cycloalkyl, or heterocycloalkyl radical, as defined herein. Aliphatic groups may be substituted with up to three suitable substituents as defined herein.

As used herein, the term "aliphatic amine" or "aliphatic amino radical" refers to any amine or amine radical in which the amine or radical nitrogen atom is bound to an sp$^3$ carbon that is part of an alkyl, cycloalkyl, or heterocycloalkyl group. Aliphatic amine groups may be substituted with up to three suitable substituents as defined herein.

The term "alkyl" refers to $C_1$-$C_{10}$ linear or branched alkyl groups (such as methyl, ethyl, n-propyl, isopropyl, n-butyl, isobutyl, sec-butyl, tert-butyl etc.) optionally substituted by 1 to 3 suitable substituents as defined herein.

The term "cycloalkyl" or "cyclyl" refers to $C_3$-$C_{12}$ mono, bicyclic or tricyclic carbocyclic ring (e.g., cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonan), etc.) that is optionally substituted by 1 to 3 suitable substituents as defined herein. Bicyclic or tricyclic species may be fused, bridged or spirocyclic. Thus, examples of "cycloalkyl" or "cyclyl" groups, as defined herein, include, but are not limited to cyclopropyl, cyclobutyl, cyclopentyl, cyclohexyl, cycloheptyl, cyclohexenyl, bicyclo[2.2.1]heptanyl, bicyclo[3.2.1]octanyl, bicyclo[3.1.0]hexyl and spiro[2.4]heptyl.

The term "heterocycloalkyl" or "heterocyclyl" or "heterocycle" refers to a mono, bicyclic or tricyclic group containing 3 to 9 carbon atoms and 1 to 4 heteroatoms selected from —N, —NR, —O—, —S—, —SO— and —SO$_2$—, wherein—unless otherwise mentioned—the cyclic radical is optionally substituted by 1 to 3 suitable substituents as defined herein. Bicyclic or tricyclic species may be fused, bridged or spirocyclic. Examples of such groups include but are not limited to azetidinyl, pyrrolidinyl, piperidinyl, morpholinyl, piperazinyl, tetrahydrofuranyl, oxetanyl, thiomorpholinyl, quinuclidinyl, 5-aza-spiro[2.4]heptyl and 3-aza-bicyclo[3.1.0] hexyl.

As used herein, the term "halogen" includes fluoro, chloro, bromo or iodo or fluoride, chloride, bromide or iodide.

As used herein, the term "carbonyl" or "(C=O)" (as used in phrases such as alkylcarbonyl, alkyl-(C=O)— or alkoxycarbonyl) refers to the joiner of the >C=O moiety to a second moiety such as an alkyl or amino group (i.e. an amido group).

When two substituents attached to a nitrogen atom [such as in —N(R1)R2 or —N(R3)R4] taken together and with inclusion of the nitrogen atom, to which they are attached, form a cyclic amine, said amine can be a mono, bicyclic or tricyclic ring comprising 3 to 9 carbon atoms and 0 to 3 further heteroatoms selected from —N—, —O—, —S—, —SO— and —SO$_2$— (excluding the nitrogen atom to which the two substituents are attached).

The cyclic amine may be optionally substituted with 1 to 3 suitable substituents as defined herein. Bicyclic or tricyclic species may be fused bridged or spirocyclic. Examples of such cyclic amines include but are not limited to morpholine, azetidine, piperazine, piperidine, pyrrolidine, indoline, thiomorpholine.

A "suitable substituent" means a functional group which is suited for its intended function. Thus, said "suitable substituent" may mean a chemically and, if desired, pharmaceutically acceptable functional group. Such suitable substituents for the aforementioned aryl, heteroaryl, alkyl, cycloalkyl, heterocycloalkyl groups may be routinely described by those skilled in the art. Illustrative examples of said suitable substituents include, but are not limited to hydrogen, halo groups, perfluoroalkyl groups, perfluoroalkoxy groups, alkyl groups, alkenyl groups, alkynyl groups, hydroxy groups, oxo groups, alkylthio groups, arylthio groups, alkylsulfonyl groups, arylsulfonyl groups, heteroarylsulfonyl groups, alkylsulfonate groups, arylsulfonate groups, perfluoroalkylsulfonate groups, alkoxy groups, aryl or heteroaryl groups, cycloalkyl or heterocycloalkyl groups, aryloxy or heteroaryloxy groups, aralkyl or heteroaralkyl groups, aralkoxy or heteroaralkoxy groups, HO—(C=O)— groups, amino groups, alkyl- and dialkylamino groups, carbamoyl groups, alkylcarbonyl groups, alkoxycarbonyl groups, alkylaminocarbonyl groups, dialkylaminocarbonyl groups, sulfonamido groups, alkylsulfonamido groups, dialkylsulfonamido groups, amido groups, N-acyl groups, arylcarbonyl groups, aryloxycarbonyl groups and the like, as well as, depending on the intended function, nitro, cyano and the like. Methylene groups may also be substituted for a carbonyl (C=O) group. Those skilled in the art will appreciate that many substituents can be substituted by additional substituents.

In general, if residues, substituents or groups occur several times in a compound they may have the same or different meanings.

The compounds and salts prepared by the methods of the present invention may exist in several isomeric forms. All isomeric forms (e.g. all stereoisomeric forms like chiral, enantiomeric, diastereomeric or racemic forms, atropisomeric, tautomeric and all geometric isomeric forms) of the compounds and salts thereof prepared by the methods of the present invention are intended within this invention, unless the specific isomer form is specifically indicated.

Thus, e.g. the compounds and salts prepared by the methods of the present invention may exist in several tautomeric forms, including the enol and imine form, and the keto and enamine form and geometric isomers and mixtures thereof. The preparation of all such tautomeric forms is included within the scope of the present invention. Tautomers exist as mixtures of a tautomeric set in solution. In solid form, usually one tautomer predominates. Even though the preparation of one tautomer may be described, the present invention encompasses the preparation of all tautomers of the present compounds.

The present invention also includes the preparation of atropisomers of the compounds prepared by methods of the present invention. Atropisomers refer to compounds that can be separated into rotationally restricted isomers.

The compounds prepared by the methods of the invention may contain olefin-like double bonds. When such bonds are present, the compounds exist as cis and trans configurations and as mixtures thereof and the present invention contemplates the preparation of such compounds.

As disclosed herein, compounds of formula III can be prepared by reaction of pyrimidine of formula I and a primary or secondary amine nucleophile of formula II in a suitable organic solvent or mixture of solvents. The meanings of X1 and X2 (which may be the same or different) on pyrimidine of formula I include those as described above. Preferentially, X1 and X2 are the same. Leaving groups X1 and X2 on pyrimidine of formula I particularly suitable for displacement include 4-nitrophenyloxy and benzotriazol-1-oxy.

It has been found for the abovementioned method according to this invention that, comparing the leaving group ability of the benzotriazol-1-oxy and the 4-nitrophenyloxy leaving group, the benzotriazol-1-oxy leaving group appears to be more reactive than the 4-nitrophenyloxy leaving group. However, depending on the reaction conditions, the benzotriazol-1-oxy leaving group can isomerize to form the N-bonded isomers. Thus, in a preferred practical embodiment of this method, the 4-nitrophenyloxy leaving group and 2,4-bis(p-nitrophenyloxy)-5-trifluoromethylpyrimidine as reactant is used.

Primary or secondary amine nucleophiles of formula II being useful in the abovementioned reaction according to this invention include those as described above. Particularly suitable amine nucleophiles of formula II for this reaction with compounds of formula I are primary aromatic amines (such as e.g. aniline derivatives) as described herein.

Suitable organic solvents for this reaction include but are not limited to tetrahydrofurane, 2-methyl-tetrahydrofurane, N-methyl-2-pyrrolidinone, and non-nucleophilic alcohols, such as e.g. tert-butanol, tert-pentanol, neo-pentanol, sec-pentanol or sec-isoamylalcohol, or mixtures thereof.

The reaction temperature for this reaction may range from about 0° C. to about 120° C., in one embodiment involving the benzotriazol-1-oxy leaving group the reaction temperature may range from ambient temperature to about 50° C., in another embodiment involving the 4-nitrophenyloxy leaving group the reaction may be conducted at elevated temperature (e.g. in a range from about 70° C. to about 120° C.). If beneficial, the reaction is run starting at lower temperature and rising the temperature to the desired higher one.

Optionally, when the benzotriazol-1-oxy leaving group is used in this reaction, an auxiliary agent such as N,O-bis(trimethylsilyl)acetamide can be used as water scavenger for the HOBt monohydrate.

The present invention also relates to processes disclosed herein, said processes may comprise methods of making and/or reacting compounds of formulae I and/or III as described herein. The present invention also relates to the intermediates (including compounds of formulae I and III as disclosed herein), including their salts, isomers and salts of these isomers.

The processes described herein may be carried out in a single step or in several sequential steps. The intermediates may be isolated or synthesized in situ, with or without purification.

Isolation and purification methods are known in the art and include, for example, removing the solvent(s), precipitation (e.g. with a co-solvent), crystallization, chromatography on a suitable support material (e.g. normal and reverse phase), extraction, trituration, and the like.

The choice of the most appropriate procedural approach in each case may be determined by a person skilled in the art on the base of his/her expert knowledge.

Illustrative amines of formula II [HN(R1)R2] which may be used in the reaction according to this invention may include—without being restricted to—toluidine (e.g. 2- or 4-methylaniline), 5-amino-1,3-dihydro-indol-2-one, chloroaniline (e.g. 3- or 4-chloroaniline), methoxyaniline (e.g. 4-methoxyaniline or 2-methoxyaniline), benzylamine, N-(4-methylbenzyl)-amine, N,N-dimethyl-1,4-phenylenediamine, cyclohexylamine, N-(cyclohexylmethyl)-amine, carboxyaniline (e.g. 4-carboxyaniline), piperidine, N-methyl-toluidine (e.g. N-methyl-p-toluidine), or the like.

It is moreover known to the person skilled in the art that if there are a number of reactive centers on a starting or intermediate compound it may be necessary to block one or more reactive centers temporarily by protective groups in order to allow a reaction to proceed specifically at the desired reaction center. A detailed description for the use of a large number of proven protective groups is found, for example, in "Protective Groups in Organic Synthesis" by T. Greene and P. Wuts (John Wiley & Sons, Inc. 2007, 4rd Ed.) or in "Protecting Groups (Thieme Foundations Organic Chemistry Series N Group" by P. Kocienski (Thieme Medical Publishers, 2004).

In the reactions described herein, any reactive groups present such as carboxy-, carbonyl-, hydroxy-, amino-, alkylamino- or imino-groups may be protected during the reaction by conventional protecting groups which are cleaved again after the reaction.

For example, a protecting group for a carboxy group may be the methyl-, ethyl-, tert.-butyl- or benzyl-group, particularly the tert.-butyl- or benzyl-group.

For example, a protecting group for a carbonyl group may be an acetal or ketal like the 1,3-dioxolane- or the 1,3-dioxane-group.

For example, a protecting group for a hydroxy group may be a trimethylsilyl-, tert.-butyldimethylsilyl-, acetyl-, trityl-, benzyl- or tetrahydropyranyl-group.

Protecting groups for an amino, alkylamino or imino group may be, for example, a formyl, acetyl, trifluoroacetyl, ethoxycarbonyl, tert.butoxycarbonyl, benzyloxycarbonyl, benzyl, methoxybenzyl or 2,4-dimethoxybenzyl group.

Thus, e.g., a suitably protected carboxyaniline within the meaning of this invention may be, for example, 4-amino-benzoic acid tert-butyl ester or 4-amino-benzoic acid benzyl ester.

The cleavage of a carboxymethyl- or a carboxyethyl-group can for example be carried out hydrolytically in an aqueous solvent, e.g. in water, methanol/water, isopropanol/water, acetic acid/water, tetrahydrofuran/water or dioxane/water, in the presence of an acid such as trifluoroacetic acid, hydrochloric acid or sulphuric acid or in the presence of an alkali base as for example lithium hydroxide, sodium hydroxide or potassium hydroxide, but preferably sodium hydroxide, or aprotically in the presence of e.g. iodotrimethylsilane, at temperatures between 0 and 120° C., preferably at temperatures between 10 and 100° C.

An acetal or ketal can be cleaved with acetic acid, trifluoroacetic acid, hydrochloric acid, sulphuric acid or pyridium-p-toluene sulfonate in mixtures with water or in organic solvents like for example dichloromethane, 1,2-dichloroethane, tetrahydrofurane, dioxane, toluene or acetone at temperatures between −20° C. and 150° C., but preferably between 0° C. and 120° C.

A benzyl, methoxybenzyl or benzyloxycarbonyl group is advantageously cleaved hydrogenolytically, e.g. with hydrogen in the presence of a catalyst such as palladium/charcoal in a suitable solvent such as methanol, ethanol, ethyl acetatetetrahydrofurane, dioxane or glacial acetic acid, optionally with the addition of an acid such as hydrochloric acid at temperatures between 0 and 100° C., but preferably at ambient temperatures between 20 and 60° C., and at a hydrogen pressure of 1 to 7 bar, but preferably 3 to 5 bar. A 2,4-dimethoxybenzyl group, however, is preferably cleaved in trifluoroacetic acid in the presence of anisole.

A tert.butyl or tert.butyloxycarbonyl group is preferably cleaved by treating with an acid such as trifluoroacetic acid or hydrochloric acid or by treating with iodotrimethylsilane optionally using a solvent such as dichloromethane, dioxane, methanol or diethylether.

A trimethylsilyl- or tert.-butyldimethylsilyl-group is cleaved with a fluoride reagent like for example tetrabutylammonium fluoride or caesium fluoride or with an acid like for example trifluoroacetic acid, hydrochloric acid or sulphuric acid in a solvent like e.g. dichloromethane, 1,2-dichloroethane, diethylether, tetrahydrofurane, dioxane, acetonitrile or toluene at temperatures between −50° C. and 120° C., but preferably between −20° C. and 80° C.

Amines of formula II or V can be provided as disclosed herein or they are known or can be obtained analogously or similarly to known procedures. Such as e.g. amines of formula V can be obtained as described in WO 2007/135036.

Compounds of formula I, in which X1 and X2 have the meanings given above, may be obtained using methods of synthesis known in principle. Preferably; compounds of formula I, in which X1 and X2 have the meanings given above (X1 and X2 may be the same or different, preferentially the same), are obtained via a process comprising nucleophilic aromatic substitution reaction of appropriate pyrimidine compounds with appropriate hydroxy compounds.

Preferably within the present invention, acidic hydroxy compounds which are known to the skilled person are used for the preparation of these compounds of formula I, in which X1 and X2 are the same or different (preferentially the same) leaving groups according to the present invention. The hydroxyl group of these hydroxy compounds can be bonded, inter alia, to a nitrogen atom or to a phenyl ring. Known acidic hydroxy compounds may include, without being restricted to, phenols (e.g. 4-nitrophenol (HOPnp) or pentafluorophenol (HOPfp)), N-hydroxy-imides (e.g. N-hydroxysuccinimide (HOSu) or N-hydroxyphthalimide (HOPh)), N-hydroxy-azoles (e.g. 1-hydroxybenzotriazole (HOBt) or 1-hydroxy-7-azabenzotriazole (HOAt)), N-hydroxy-azinones (cyclic N-hydroxy-amides) (e.g. 3-hydroxy-1,2,3-benzotriazin-4 (3H)-one (HOOBt, HODhbt)) and the like.

Particular appropriate hydroxy compounds used are 1-hydroxybenzotriazole (HOBt) and, especially, 4-nitrophenol (HOPnp).

Pyrimidine compounds which can be used for the preparation of these compounds of formula I, in which X1 and X2 are the same or different (preferentially the same) leaving groups according to the present invention, are those compounds of formula I' wherein both X are the same or different (preferentially the same) leaving groups, which may independently selected from the group consisting of halide, arylsulfonate, alkylsulfonate, perfluoroalkylsulfonate, arylsulfinate and alkylsulfinate, such as particularly 2,4-dichloro-5-trifluoromethylpyrimidine.

Thus, for example, compounds of formula I, in which
X1 is a leaving group selected from the group consisting of:
phenyloxy optionally substituted by 1-5 suitable substituents,
heterocyclyl N-oxy optionally substituted by 1-5 suitable substituents, and
heteroaryl N-oxy optionally substituted by 1-5 suitable substituents,
and X2 is identical with X1,
can be prepared by reacting compounds of formula I', in which both X are the same or different (preferentially the same) and are each independently halides, such as e.g. 2,4-dichloro-5-trifluoromethylpyrimidine,
with the corresponding hydroxy compound of formula X1-H.

In more detailed example, compounds of formula I, in which X1 and X2 are the same leaving group as described herein, can be obtained from compounds of formula I', particularly 2,4-dichloro-5-trifluoromethylpyrimidine (typically in an amount of 1.0 equivalent) and the corresponding hydroxy compound (e.g. in an amount of 1.0-2.4 equivalents, typically 1.6-2.4 equivalents), particularly HOPnp or HOBt, analogously or similarly as described in the following examples, such as in the presence of a suitable inorganic or, especially, organic auxiliary base, preferably a non-nucleophilic base, such as e.g. a tertiary amine, e.g. triethylamine, N,N-diisopropyl-ethylamine, or the like (typically in an amount of 0.9-2.3 equivalents), particularly DIPEA, in a suitable organic solvent or mixture of solvents, such as e.g. tetrahydrofurane, 1,4-dioxan, 2-methyl-tetrahydrofurane, N-methyl-2-pyrrolidinone, dimethyl fomamide, dimethylacetamide, dimethyl sulfoxide or a non-nucleophilic alcohol, e.g. tert-butanol, tert-pentanol, neo-pentanol, sec-pentanol or sec-isoamylalcohol, or mixtures thereof at a suitable reaction temperature which preferably range from 0° C. to 70° C. If beneficial, the reaction is run starting at lower temperature and rising the temperature to the desired higher one.

Within a process of this invention, compounds of formula I obtained may be isolated or carried on without isolation to the reaction with amines of formula II as described herein, such as e.g. via a one-pot reaction by adding amines of formula II (typically 1.0-1.3 equivalents) to the reaction mixture obtained and reacting to form compounds of formula III.

In a preferred embodiment of this process according to this invention, relative to the amount of 2,4-dichloro-5-trifluoromethylpyrimidine, 1.6-2.4 equivalents (typically a slight excess) of 4-nitrophenole and 1.5-2.3 equivalents (typically a slight deficit) of said suitable base (typically N,N-diisopropyl-ethylamine) are used to obtain 2,4-bis(p-nitrophenyloxy)-5-trifluoromethylpyrimidine, which is carried on—preferably without being isolated—to nucleophilic aromatic substitution reaction according to this invention by adding a slight excess, preferably 1.0-1.3 equivalents, of an aromatic amine to the reaction mixture and reacting to form the corresponding 2-amino-4-(p-nitrophenyloxy)-5-trifluoromethylpyrimidine derivative as major isomer.

Compounds of formula I' wherein both X are the same or different leaving groups independently selected from the group consisting of halide, arylsulfonate, alkylsulfonate, perfluoroalkylsulfonate, arylsulfinate and alkylsulfinate are known or can be obtained analogously or similarly to known procedures (e.g., a preparation of 2,4-dichloro-5-trifluoromethylpyrimidine is described in WO 2005/0123780).

Compounds of formula III, when reacted with an oxygen, sulfur or nitrogen nucleophile (such as e.g. with primary or secondary amines of formula V [HN(R3)R4], in which R3 and R4 are substituents independently selected from the group consisting of hydrogen, an aromatic group and an aliphatic group; or R3 and R4 taken together and with inclusion of the nitrogen atom to which they are attached form a 4-11 membered aromatic or aliphatic ring, to provide 2,4-diamino products of formula III' in which X is —N(R3)R4), are useful intermediates in the preparation of pharmacological active compounds, such as e.g. protein kinase inhibitors which may be useful in the treatment of abnormal cell growth, such as cancer, in mammals. Compounds such as these are described, for example, in WO 03/030909, WO 03/032997, WO 03/078404, WO 2004/046118, WO 2004/048343, WO 2004/056807, WO 2004/056786, WO 2005/026130, WO 2005/049033, WO 2005/111023, WO 2005/113515, WO2006/021544, US 2006/025433, WO 2006/074057, WO 2006/091737, WO 2006/099974, WO 2006/117560, WO 2007/003596, WO 2007/049041, WO 2007/063384, WO 2007/072158, WO 2007/096351, WO 2007/115999, US 2007/203161, WO 2007/132010, WO 2007/140957 and WO 2008/003766.

The present invention is not to be limited in scope by the specific embodiments described herein. Various modifications of the invention in addition to those described herein may become apparent to those skilled in the art from the present disclosure. Such modifications are intended to fall within the scope of the appended claims.

All patent applications cited herein are hereby incorporated by reference in their entireties.

Further embodiments, features and advantages of the present invention may become apparent from the following examples. The following examples serve to illustrate, by way of example, the principles of the invention without restricting it.

EXAMPLES

Preparation of 2,4-bis(p-nitrophenyloxy)-5-trifluoromethylpyrimidine 12.8 g p-Nitrophenol is added to a solution of 10.0 g 2,4-dichloro-5-trifluoromethylpyrimidine in 50 mL N-methyl-2-pyrrolidinone at ambient temperature. 11.9 g diisopropyl ethyl amine is added (exothermic reaction). The reaction mixture is stirred for 8 hours at 50° C. The solution is cooled to 5° C. 50 mL of purified water is added. The suspension is stirred for 30 min at 5° C. The precipitate is filtered and washed with purified water and tert.-butyl methyl ether. After drying in a vacuum drying cupboard 19.7 g of crude product is obtained as yellowish solid.

For further purification the crude product is suspended in 75 mL tert.-butyl methyl ether and stirred for 1 hour under cooling in an ice bath. After filtering and drying in a vacuum drying cupboard 17.0 g of product is obtained.

To get pure material 5 g of the obtained product is dissolved in 50 mL ethyl acetate. 5 ml of hydrochloric acid (3%) is added and the phases are separated. The organic phase is washed with purified water, sodium carbonate solution (5%) and purified water. After evaporation of the organic phase 4.43 g of product as yellowish solid is obtained.

HPLC: $R_t$=4.7 min

[Column: Inertsil ODS-3, 3 µm; dimension: 2.1×50 mm; mobile phase: A: water/0.1% formic acid, B: acetonitrile/0.1% formic acid; gradient: from A/B (80:20) to A/B (10:90) in 6 min. hold for 1.5 min at A/B (10:90); flow rate: 1 mL/min; detection UV 254 nm and 297 nm; temperature 40° C.]

Process According to the Invention Comprising Using the p-nitrophenyloxy Leaving Group
Version 1:

8.0 mL Diisopropyl ethyl amine (DIPEA) is added slowly to a solution of 5 g 2,4-dichloro-5-trifluoromethylpyrimidine and 7.0 g p-nitrophenol in 15 mL N-methyl-2-pyrrolidinone (exothermic reaction). The solution is stirred for 1 hour at ambient temperature. 5.8 g 4-amino-benzoic acid benzyl ester is added. The reaction mixture is heated at 100 to 115° C. for 17 hours. After cooling to ambient temperature, ethyl acetate and purified water are added. The organic phase is separated and washed with purified water, with an aqueous citric acid solution (10%) and with a sodium chloride solution. The organic phase is dried over sodium sulphate. The solvent is evaporated under reduced pressure. 18.7 g of a brownish solid is obtained. The crude mixture is separated via chromatography on 1.2 kg Alox (activity 2). As eluent cyclohexane/ethyl acetate mixtures (5:1 to 1:1) are used. Pure fractions are collected and evaporated under reduced pressure. As products are obtained:

0.25 g 4-amino pyrimidine derivative $R_t$ (HPLC)=5.2 min 2.8 g 2-amino pyrimidine derivative $R_t$ (HPLC)=5.6 min

[Column: Inertsil ODS-3, 3 µm; dimension: 2.1×50 mm; mobile phase: A: water/0.1% formic acid, B: acetonitrile/0.1% formic acid; gradient: from A/B (80:20) to A/B (10:90) in 6 min. hold for 1.5 min at A/B (10:90); flow rate: 1 mL/min; detection UV 254 nm and 297 nm; temperature 40° C.]

Version 2:

29.8 g Diisopropyl ethyl amine (DIPEA) is added slowly to a solution of 25 g 2,4-dichloro-5-trifluoromethylpyrimidine and 35.3 g p-nitrophenol in 100 mL N-methyl-2-pyrrolidinone (exothermic reaction). The solution is stirred for 1 hour at ambient temperature. 31.4 g 4-amino-benzoic acid benzyl ester is added. The reaction mixture is heated at 90 to 100° C. for 24 hours. [selectivity (HPLC area % at 254 nm): 4-amino pyrimidine derivative 8%, 2-amino pyrimidine derivative 85%, 2,4-diamino pyrimidine derivative ($R_t$=6.2 min) 7%]. 29.8 g diisopropyl ethyl amine and 24.5 g cispentacin-isopropylamide are added. The reaction mixture is heated at 90° C. to 100° C. for 20 hours. At 85 to 90° C. a mixture of 300 mL iso-propanol and 100 mL 2-methyl-tetrahydrofurane is added slowly to the reaction mixture. The suspension is stirred under cooling to ambient temperature for 20 hours. The precipitate is filtered, washed with iso-propanol and subsequently with tert.-butyl methyl ether (TBME). After drying 42.2 g (68%) of the product is obtained as colourless solid.

$R_t$ (HPLC)=5.2 min

[Column: Inertsil ODS-3, 3 µm; dimension: 2.1×50 mm; mobile phase: A: water/0.1% formic acid, B: acetonitrile/0.1% formic acid; gradient: from A/B (80:20) to A/B (10:90) in 6 min. hold for 1.5 min at A/B (10:90); flow rate: 1 mL/min; detection UV 254 nm and 297 nm; temperature 40° C.]

Process According to the Invention Comprising Using the benzotriazol-1-oxy Leaving Group A solution of 2.49 g 1-hydroxy-1H-benzotriazol hydrate and 2.14 g diisopropyl ethyl amine in 11 mL 2-methyltetrahydrofuran/N-methyl-2-pyrrolidinone (1:1) is slowly added to a solution of 2.0 g 2,4-dichloro-5-trifluoromethylpyrimidine in 5 mL 2-methyltetrahydrofuran/N-methyl-2-pyrrolidinone (1:1) under cooling so that the temperature is kept below 10° C. 4 mL 2-methyltetrahydrofuran is added and the reaction mixture is stirred for 1 hours at 10° C. 3.94 g N,O-bis(trimethylsilyl)acetamide (water scavenging) and 2.1 g 4-amino-benzoic acid benzyl ester are added. The reaction mixture is stirred for 1.5 hours at 10° C. and subsequently for 20 hours at 20° C. and 4 hours at 40° C. to 50° C. 1.65 g cispentacin-isopropylamide and 2.6 g diisopropyl ethyl amine are added. The reaction mixture is heated at 80° C. to 90° C. for 2 hours. Heating is stopped and 50 mL of methanol is added. The reaction mixture is stirred for 16 hours under cooling to ambient temperature. The precipitate is filtered, washed with methanol and with tert.-butyl methyl ether (TBME). After drying 3.40 g (68%) of the product is obtained as colourless solid.

The invention claimed is:

1. A method for making a compound of formula III

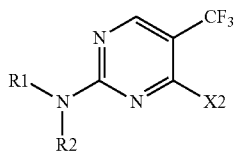
(III)

wherein
X2 is a leaving group, and
R1 and R2 are substituents independently selected from hydrogen, an aromatic group and an aliphatic group, or taken together —N(R1)R2 can form a 4-11 membered aromatic or aliphatic ring,
comprising reacting a compound of formula I

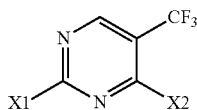
(I)

with an amine of formula II [HN(R1)R2] to form a compound of formula III,
wherein
X1 is a leaving group selected from the group consisting of:
phenyloxy optionally substituted by 1-5 suitable substituents,
heterocyclyl N-oxy optionally substituted by 1-5 suitable substituents, and
heteroaryl N-oxy optionally substituted by 1-5 suitable substituents;
wherein said aromatic group, aliphatic group, or aromatic or aliphatic ring may be substituted with 1-3 suitable substituents selected from hydrogen, halo groups, perfluoroalkyl groups, perfluoroalkoxy groups, alkyl groups, alkenyl groups, alkynyl groups, hydroxy groups, oxo groups, alkylthio groups, arylthio groups, alkylsulfonyl groups, arylsulfonyl groups, heteroarylsulfonyl groups, alkylsulfonate groups, arylsulfonate groups, perfluoroalkylsulfonate groups, alkoxy groups, aryl and heteroaryl groups, cycloalkyl and heterocycloalkyl groups, aryloxy and heteroaryloxy groups, aralkyl and heteroaralkyl groups, aralkoxy and heteroaralkoxy groups, HO—(C=O)— groups, amino groups, alkyl- and dialkylamino groups, carbamoyl groups, alkylcarbonyl groups, alkoxycarbonyl groups, alkylaminocarbonyl groups, dialkylaminocarbonyl groups, sulfonamido groups, alkylsulfonamido groups, dialkylsulfonamido groups, amido groups, N-acyl groups, arylcarbonyl groups, aryloxycarbonyl groups, nitro and cyano.

2. The method of claim 1 wherein X1 and X2 are the same or different leaving groups independently selected from 2- or 4-nitrophenyloxy, pentafluorophenyloxy, N-succinimidoxy, N-phthalimidoxy, benzotriazol-1-oxy, 7-aza-benzotriazol-1-oxy and 1,2,3-benzotriazin-4(3H)-one-3-oxy.

3. The method of claim 1 wherein X2 is the same as X1.

4. The method of claim 1 wherein one of R1 and R2 is hydrogen and the other is an aromatic group.

5. The method of claim 1 wherein X1 and X2 are the same and are 4-nitrophenyloxy.

6. The method of claim 1 wherein X1 and X2 are the same and are benzotriazol-1-oxy.

7. The method of claim 5 wherein said reaction is conducted at a reaction temperature from about 70° C. to about 120° C.

8. The method of claim 6 wherein wherein said reaction is conducted at a reaction temperature from about 0° C. to about 50° C.

9. The method of claim 1 characterized in that said reaction is conducted without any Lewis acidic metal cation.

10. The method of claim 1 further comprising the step of reacting the compound of formula III with an oxygen, sulphur or nitrogen nucleophile.

11. The method of claim 1 wherein the amine of formula II is 4-amino-benzoic acid benzyl ester.

12. The method of claim 1 wherein said reaction is conducted in an organic solvent or mixture of solvents.

13. The method of claim 12 wherein said reaction is conducted in an organic solvent selected from tetrahydrofurane, 2-methyl-tetrahydrofurane, N-methyl-2-pyrrolidinone, tert-butanol, tert-pentanol, neo-pentanol, sec-pentanol, sec-isoamylacohol, and mixtures thereof.

* * * * *